United States Patent
Bharat et al.

(10) Patent No.: US 9,867,998 B2
(45) Date of Patent: Jan. 16, 2018

(54) CALIBRATION APPARATUS

(71) Applicants: KONINKLIJKE PHILIPS N.V., Eindhoven (NL); SUNNYBROOK HEALTH SCIENCES CENTRE, Toronto (CA)

(72) Inventors: Shyam Bharat, Cortlandt Manor, NY (US); Jochen Kruecker, Washington, DC (US); Ananth Ravi, Toronto (CA); Ehsan Dehghan Marvast, New York, NY (US)

(73) Assignees: Koninkljke Philips N.V., Eindhoven (NL); Sunnybrook Research Institute, Toronto, Ontario (CA)

( * ) Notice: Subject to any disclaimer, the term of this patent is extended or adjusted under 35 U.S.C. 154(b) by 27 days.

(21) Appl. No.: 14/443,662

(22) PCT Filed: Nov. 20, 2013

(86) PCT No.: PCT/IB2013/060261
§ 371 (c)(1),
(2) Date: May 19, 2015

(87) PCT Pub. No.: WO2014/087289
PCT Pub. Date: Jun. 12, 2014

(65) Prior Publication Data
US 2015/0306425 A1    Oct. 29, 2015

Related U.S. Application Data

(60) Provisional application No. 61/733,988, filed on Dec. 6, 2012.

(51) Int. Cl.
*A61N 5/10*    (2006.01)
*A61B 8/08*    (2006.01)
(Continued)

(52) U.S. Cl.
CPC .......... *A61N 5/1039* (2013.01); *A61B 8/0841* (2013.01); *A61B 34/20* (2016.02);
(Continued)

(58) Field of Classification Search
CPC .. G06T 7/337; G06T 7/97; G06T 7/70; A61B 90/39; A61B 2090/363; A61B 1/00057; A61N 5/1027
See application file for complete search history.

(56) References Cited

U.S. PATENT DOCUMENTS 6,024,690 A    2/2000    Lee et al.
6,112,113 A *  8/2000    Van Der Brug ....... A61B 90/36
                                                                    600/427
(Continued)

FOREIGN PATENT DOCUMENTS

EP    1997531 A1    3/2008
JP    2012073192 A  4/2012

OTHER PUBLICATIONS

Ayvaci, A. et al. "Biopsy needle detection in transrectal ultrasound", Computerized Medical Imaging and Graphics 35 (2011) 653-659.
(Continued)

*Primary Examiner* — Iman K Kholdebarin
*Assistant Examiner* — Mai Tran

(57) ABSTRACT

The invention relates to a calibration apparatus for calibrating a system for introducing an influencing element like a radiation source into an object, particularly for calibrating a brachytherapy system. First and second images show a longish introduction device (12) like a catheter and a tracking device (16) like an electromagnetically trackable guidewire inserted into the introduction device as far as possible, and the introduction device and a calibration element (46) having the same dimensions as the influencing element and being inserted into the introduction device as far as possible. A spatial relation between the tracking device and the calibration element is determined based on the images for
(Continued)

calibrating the system. Knowing this spatial relation allows accurately determining an influencing plan like a brachytherapy treatment plan and accurately positioning the influencing element in accordance with the influencing plan, which in turn allows for a more accurate influencing of the object.

15 Claims, 11 Drawing Sheets

(51) Int. Cl.
    *A61B 34/20*     (2016.01)
    *G06T 7/80*     (2017.01)
    *G06T 7/00*     (2017.01)
    *G06T 7/33*     (2017.01)
    *G06T 7/70*     (2017.01)
    *A61B 90/00*     (2016.01)

(52) U.S. Cl.
    CPC ............ *A61B 90/39* (2016.02); *A61N 5/1001* (2013.01); *A61N 5/103* (2013.01); *A61N 5/1027* (2013.01); *A61N 5/1075* (2013.01); *G06T 7/337* (2017.01); *G06T 7/70* (2017.01); *G06T 7/80* (2017.01); *G06T 7/97* (2017.01); *A61B 2034/2051* (2016.02); *A61B 2034/2061* (2016.02); *A61B 2090/363* (2016.02); *A61B 2090/3925* (2016.02); *A61B 2090/3966* (2016.02); *A61B 2560/0223* (2013.01); *G06T 2207/10132* (2013.01); *G06T 2207/30081* (2013.01)

(56) References Cited

U.S. PATENT DOCUMENTS

| | | |
|---|---|---|
| 6,283,910 B1 | 9/2001 | Bradshaw et al. |
| 6,506,145 B1 | 1/2003 | Bradshaw et al. |
| 6,846,282 B1 | 1/2005 | Ford |
| 7,229,401 B2 | 6/2007 | Kindlein |
| 7,853,312 B2 | 12/2010 | Thornton |
| 8,082,023 B2 | 12/2011 | Yarnall et al. |
| 8,721,514 B2 | 5/2014 | Shechter |
| 9,101,395 B2 | 8/2015 | Gutierrez et al. |
| 2003/0065260 A1 | 4/2003 | Cheng et al. |
| 2003/0233123 A1 | 12/2003 | Kindlein et al. |
| 2007/0129593 A1* | 6/2007 | Gueye .................. A61N 5/1027 600/7 |
| 2008/0216239 A1 | 9/2008 | Luginbuhl et al. |
| 2010/0288934 A1 | 11/2010 | Keppel et al. |
| 2013/0090554 A1 | 4/2013 | Zvuloni et al. |
| 2013/0102891 A1 | 4/2013 | Binnekamp et al. |
| 2014/0005465 A1 | 1/2014 | Ribbing |
| 2014/0094690 A1* | 4/2014 | Tolkowsky .......... A61B 5/7425 600/424 |
| 2014/0357977 A1 | 12/2014 | Zhou |

OTHER PUBLICATIONS

Ron Alterovitz et al., "Optimization of HDR brachytherapy dose distributions using linear programming with penalty costs", Medical Physics, (200611), vol. 33, No. 11, pp. 4012-4019.

\* cited by examiner

CALIBRATION APPARATUS

CROSS-REFERENCE TO PRIOR APPLICATIONS

This application is the U.S. National Phase application under 35 U.S.C. §371 of International Application Serial No. PCT/IB2013/060261, filed on Nov. 20, 2013, which claims the benefit of U.S. Application Ser. No. 61/733,988, filed on Dec. 6, 2012. These applications are hereby incorporated by reference herein.

FIELD OF THE INVENTION

The invention relates to a calibration apparatus, a calibration method and a calibration computer program for calibrating a system for introducing an influencing element into an object, wherein the influencing element is adapted to influence a target region within the object. The invention particularly relates to a calibration apparatus, a calibration method and a calibration computer program for calibrating a brachytherapy system. The invention relates further to an influencing plan determination apparatus, an influencing plan determination method and an influencing plan determination computer program for determining an influencing plan for influencing a target region within the object. The influencing plan is preferentially a treatment plan for a brachytherapy procedure.

BACKGROUND OF THE INVENTION

During a clinical high dose rate (HDR) brachytherapy procedure catheters are inserted into a target region within a person, wherein through the inserted catheters radiation sources are introduced into the target region in accordance with a treatment plan, which defines dwell times and dwell locations, for treating the target region. The treatment plan is determined in advance based on, inter alia, three-dimensional poses and shapes of the inserted catheters, wherein for determining the three-dimensional poses and shapes of the catheters within the person a user introduces sequentially a guidewire into the catheters, while the position of the tip of the guidewire within the respective catheter is electromagnetically tracked. Thus, the treatment plan, particularly the dwell positions, is determined based on, inter alia, the electromagnetically tracked positions of the tip of guidewire. Determining the treatment plan based on the positions of the tip of the guidewire within the respective catheter and also delivering the treatment based on, inter alia, the electromagnetically tracked positions of the tip of the catheter can be inaccurate, thereby reducing the quality of the brachytherapy.

SUMMARY OF THE INVENTION

It is an object of the present invention to provide a calibration apparatus, a calibration method and a calibration computer program for calibrating a system for introducing an influencing element into an object, wherein the influencing element is adapted to influence a target region within the object, which allows for a more accurate influencing of the target region. The invention relates further to an influencing plan determination apparatus, an influencing plan determination method and an influencing plan determination computer program, which allow for a determination of a more accurate influencing plan.

In a first aspect of the present invention a calibration apparatus for calibrating a system for introducing an influencing element into an object is presented, wherein the influencing element is adapted to influence a target region within the object and wherein the calibration apparatus comprises:

an image providing unit for providing a first image showing a longish introduction device, which is adapted to be inserted into the object for introducing the influencing element into the object, and a tracking device, which is adapted to track the introduction device and to be inserted into the introduction device as far as possible, and a second image showing the introduction device and a calibration element, which has the same dimensions as the influencing element and which is adapted to be inserted into the introduction device as far as possible, an identification unit for identifying the tip of the introduction device, the tracking device and the calibration device in the first and second images, a spatial relation determining unit for determining a spatial relation between the tracking device and the calibration element from the first and second images, in which the tip of the introduction device, the tracking device and the calibration element have been identified.

If immediately before the influencing element is inserted into the introduction device the tracking device is inserted into the introduction device as far as possible and if the position of the tracking device at the corresponding furthest position is determined, this determined furthest position of the tracking device can be used together with the spatial relation between the tracking device and the calibration element, which has been determined in advance in a calibration step by the calibration apparatus, for determining an influencing plan and for introducing the influencing element in accordance with the determined influencing plan. For instance, a distance between the position of a tip of the introduction device and a furthest position of the tracking device and a further distance between the position of the tip of the introduction device and a furthest position of the calibration element determined in a previous calibration step by using the calibration apparatus can be used for determining the distance between the furthest position of the tracking device and the furthest possible position of the influencing element within the introduction device, wherein this distance can be used for determining the furthest possible position of the influencing element within the introduction device based on the actually determined furthest position of the tracking device within the introduction device. This furthest possible position of the influencing element within the introduction device can be used for more accurately determining the influencing plan and for more accurately positioning the influencing element in accordance with the influencing plan, which allows for an improved influencing of the target region.

The influencing element is preferentially a radiation source for performing a brachytherapy. Correspondingly, the calibration apparatus is preferentially a brachytherapy calibration apparatus for calibrating a brachytherapy system. Moreover, the calibration element is preferentially a dummy radiation source, which has the same dimensions as the radiation source used for performing the brachytherapy. The image providing unit is preferentially adapted to provide radiographic images, i.e. x-ray images, as the first and second images, and the tracking device is preferentially an electromagnetic (EM) tracking device or a fiber optical shape sensing and localization (FOSSL) tracking device. The image providing unit can also be adapted to provide other kinds of first and second images like ultrasound images, computed tomography images, et cetera. The object is preferentially a living object like a person or an animal, wherein the target region can be a region to be treated. The influencing plan is therefore preferentially a treatment plan for treating the target region within the living object. The target region is, for instance, a prostate or a part of a prostate of a person.

The image providing unit is preferentially a storing unit, in which the first and second images can be stored and from which these images can be retrieved for providing the same. The image providing unit can also be a receiving unit for receiving the images via a wired or wireless data connection from an image generating system like an x-ray imaging system, wherein the image providing unit is adapted to provide the received images. The image providing unit can also be an image generating system itself.

Preferentially several introduction devices are inserted into the living object, in order to introduce several influencing elements along different paths into the object. The one or several introduction devices are preferentially catheters or needles.

The identification unit is preferentially adapted to automatically identify the tip of the introduction device, the tracking device and the calibration element or to allow a user to identify the tip of the introduction device, the tracking device and the calibration element. For automatically identifying these components known segmentation algorithms can be used, which may be based on, for instance, thresholding.

In an embodiment the spatial relation determining unit is adapted to determine a distance between the position of the tip of the introduction device and the position of the tracking device from the first image, in which the tip of the introduction device and the tracking device have been identified, a distance between the position of the tip of the introduction device and the position of the calibration element from the second image, in which the tip of the introduction device and the calibration element have been identified, and a distance between the position of the tracking device and the position of the calibration element based on the determined distance between the position of the tip of the introduction device and the position of the tracking device and the distance between the position of the tip of the introduction device and the position of the calibration element. This allows accurately determining the spatial relation between the tracking device and the calibration element, in particular, between the tip of the tracking device and the calibration element, in a relatively simple way.

The calibration apparatus may also comprise an ultrasound image providing unit for providing an ultrasound image of the tip of the introduction device and a tracking device position providing unit for providing a position of the tracking device, when it has been inserted into the introduction device as far as possible, wherein the identification unit is adapted to identify the tip of the introduction device in the ultrasound image and wherein the spatial relation determination unit is adapted to update the spatial relation between the tracking device and the calibration element, especially the offset between the tip of the introduction device and the tracking device, based on the ultrasound image with the identified tip of the introduction device and the provided position of the tracking device. Thus, after the spatial relations have been determined in an initial calibration step, for instance, before a brachytherapy system or parts of the brachytherapy system are used for the first time, in a later quality assurance step the spatial relation between the tracking device and the calibration element determined during the initial calibration can be updated based on ultrasound images, which are preferentially used during an actual brachytherapy. In particular, the ultrasound image with the identified tip of the introduction device and the provided position of the tracking device can be used together with the distance between the position of the tip of the introduction device and the position of the calibration element determined during the initial calibration for updating the distance between the position of the tracking device and the position of the calibration element. For this quality assurance step the imaging modality, which has been used for performing the initial calibration, like the x-ray imaging system is not needed. The quality assurance procedure can account for mechanical wear and tear or other physical changes occurring over time of the equipment involved, which may result in changes in the spatial relations between the introduction device, the tracking device and/or the influencing element. Performing this quality assurance procedure periodically, for instance, per procedure, daily, every three months, annually et cetera, can ensure that the quality of the brachytherapy remains high over time.

The ultrasound image providing unit can be a storing unit, in which the ultrasound image is stored and from which the ultrasound image can be retrieved for providing the same. The ultrasound image providing unit can also be a receiving unit for receiving the ultrasound image via a wired or wireless data connection from an ultrasound image generation device, wherein the ultrasound image providing unit is adapted to provide the received ultrasound image. The ultrasound image providing unit can also be the ultrasound image generation device itself. The ultrasound image providing unit is preferentially adapted to provide a transrectal ultrasound (TRUS) image. Using a TRUS image allows generating an ultrasound image with an ultrasound transducer being close to the prostate such that TRUS image is particularly preferred, if one or several influencing elements are to be introduced into the prostate of a person.

The ultrasound image providing unit can also be adapted to provide another kind of ultrasound image like a transabdominal, a transurethral or a transperineal ultrasound image.

Also the tracking device position providing unit can be a storing unit, wherein in this case the storing unit is adapted to store a tracking device position and to retrieve the stored tracking device position for providing the same. Moreover, the tracking device position providing unit can also be a receiving unit for receiving a tracking device position from a tracking system via a wired or wireless data connection, wherein the tracking device position providing unit can be adapted to provide the received position. The tracking device position providing unit can also be the tracking system itself.

It is further preferred that the tracking device position providing unit is adapted to provide an EM- or FOSSL-tracked position of the tracking device. Tracking the position of the tracking device by using EM tracking or FOSSL tracking allows determining the position of the tracking device with very high accuracy, thereby further improving the determination of an influencing plan and the performance of an influencing procedure like a brachytherapy, which are based on the position of the tracking device.

In a preferred embodiment the tracking device position providing unit is adapted to provide the positions of the tracking device, while it is moved inside the introduction device towards and/or away from a furthest position within the introduction device, wherein the calibration apparatus further comprises a length determination unit for determining a length of the introduction device based on the provided positions. It is therefore not necessary to deduce the length of the introduction device from, for instance, a manual measurement of the introduction device outside of the living object and an ultrasound based measurement of the introduction device within the living object. The length of the introduction device can be determined in a simpler way by using the same procedure, which is already used for determining the pose and shape of the introduction device, i.e. it is not necessary to perform two different separate procedures for determining the length of the introduction device and for determining the pose and shape of the introduction device within the living object.

In a further aspect of the present invention a calibration device for calibrating a system for introducing an influencing element into an object is presented, wherein the influencing element is adapted to influence a target region within the object and wherein the calibration device comprises a radiolucent block with radiopaque fiducials identifiable in radiographic images and a channel for receiving an introduction device that is adapted to be inserted into the object for introducing an influencing element into the object. It is preferred that at least some of the fiducials are arranged in parallel to the channel. It is further preferred that the block comprises several channels having different diameters. The block may further comprise a fixing unit for fixing the introduction device within the channel in place. Moreover, the block may comprise a tracking sensor for tracking the position of the block. The tracking sensor is, for instance, an electromagnetic tracking sensor. In a preferred embodiment the block is ultrasound compatible. This allows using the calibration device also for the ultrasound based quality assurance procedure.

In another aspect of the present invention an influencing plan determination apparatus for determining an influencing plan for influencing a target region within an object is presented, wherein the apparatus comprises:

a tracking device position providing unit for providing positions of a tracking device within an introduction device, which has been inserted into the object for introducing an influencing element into the object, wherein the positions are determined along the length of the introduction device and at a furthest position within the introduction device, an introduction device pose and shape determination unit for determining the pose and shape of the introduction device from the provided positions of the tracking device, a target region pose and shape providing unit for providing the pose and shape of the target region within the object, an influencing plan determination unit for determining the influencing plan depending on the pose and shape of the introduction device, the pose and shape of the target region, the furthest position of the tracking device within the introduction device and the spatial relation between the tracking device and the calibration element determined by the calibration apparatus as defined in claim 1.

Since the influencing plan is determined based on, inter alia, the spatial relation between the tracking device and the calibration element determined by the calibration apparatus, the influencing plan can be determined with improved accuracy, which allows for an improved quality of a subsequent influencing procedure like a subsequent brachytherapy performed in accordance with the influencing plan.

The target region pose and shape providing unit can be adapted to determine the pose and shape of the target region depending on a received image of the object like a received ultrasound image, which shows the target region within the object. The target region pose and shape providing unit can be adapted to perform a segmentation algorithm for automatically or semi-automatically segmenting the target region for providing the pose and shape of the same. However, the target region pose and shape providing unit can also be a storing unit, in which the pose and shape of the target region is stored already and from which the pose and shape of the target region can be retrieved for providing the same. The target region pose and shape providing unit can also be a receiving unit for receiving the pose and shape of the target region from another device for determining the same, wherein the target region pose and shape providing unit can be adapted to provide the received pose and shape of the target region.

In a further aspect of the present invention a calibration method for calibrating a system for introducing an influencing element into an object is presented, wherein the influencing element is adapted to influence a target region within the object and wherein the calibration method comprises:

providing a first image showing a longish introduction device, which is adapted to be inserted into a living object for introducing an influencing element within the living object, and a tracking device, which is adapted to track the introduction device and which is inserted into the introduction device as far as possible, and a second image showing the introduction device and a calibration element, which has the same dimensions as influencing element and which is inserted into the introduction device as far as possible, by an image providing unit, identifying the tip of the introduction device, the tracking device and the calibration element in the first and second images by an identification unit, determining a spatial relation between the tracking device and the calibration element from the first and second images, in which the introduction device, the tracking device and the calibration element have been identified, by a spatial relation determining unit.

In a further aspect of the present invention an influencing plan determination method for determining an influencing plan for influencing a target region within an object is presented, wherein the influencing plan determination method comprises:

providing positions of a tracking device within an introduction device, which has been inserted into the object for introducing an influencing element into the object, by a tracking device position providing unit, wherein the positions have been determined along the length of the introduction device and at a furthest position within the introduction device, determining the pose and shape of the introduction device from the provided positions of the tracking device by an introduction device pose and shape determination unit, providing the pose and shape of the target region within the object by a target region pose and shape providing unit, determining the influencing plan depending on the pose and shape of the introduction device, the pose and shape of the target region, the furthest position of the tracking device within the respective introduction device and the spatial relation between the tracking device and the calibration element determined by the calibration apparatus as defined in claim 1 by an influencing plan determination unit.

In another aspect of the present invention a calibration computer program for calibrating a system for introducing an influencing element into an object is presented, wherein the influencing element is adapted to influence a target region within the object and wherein the calibration computer program comprises program code means for causing a calibration apparatus as defined in claim 1 to carry out the steps of the calibration method as defined in claim 12, when the calibration computer program is run on a computer controlling the calibration apparatus.

In a further aspect of the present invention an influencing plan determination computer program for determining an influencing plan for influencing a target region within an object is presented, wherein the influencing plan determination computer program comprises program code means for causing an influencing plan determination apparatus as defined in claim 11 to carry out the steps of the influencing plan determination method as defined in claim 13, when the influencing plan determination computer program is run on a computer controlling the influencing plan determination apparatus.

It shall be understood that the calibration apparatus of claim 1, the calibration device of claim 7, the influencing plan determination apparatus of claim 11, the calibration method of claim 12, the influencing plan determination method of claim 13, the calibration computer program of claim 14 and the influencing plan determination computer program of claim 15 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
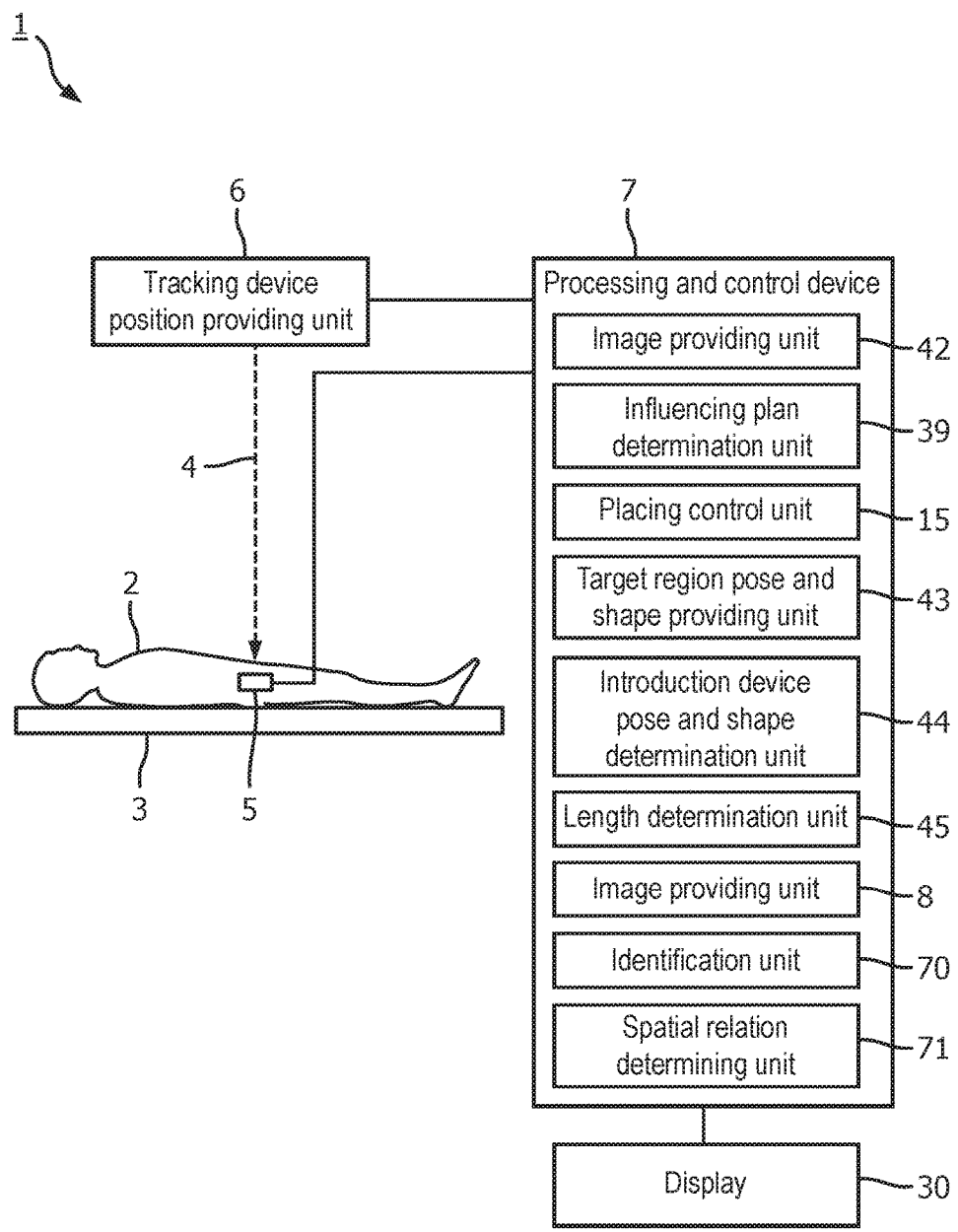
FIG. 1 shows schematically and exemplarily an embodiment of a brachytherapy system.
Figure 2:
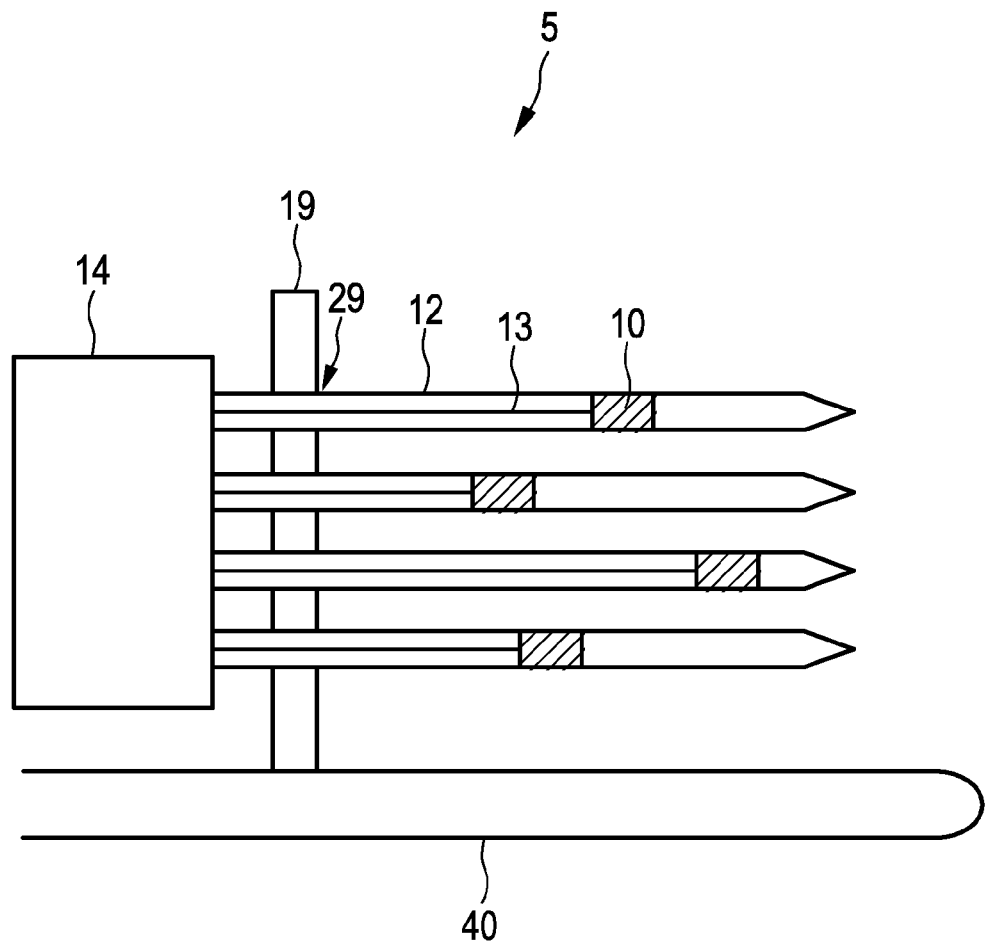
FIG. 2 shows schematically and exemplarily a placing unit of the brachytherapy system.

FIG. 1 schematically and exemplarily shows a system for introducing an influencing element into an object, wherein the influencing element is adapted to influence a target region within the object. In this embodiment the system is a brachytherapy system 1 for applying a brachytherapy to a target region within a person 2 lying on a table 3. The brachytherapy system 1 comprises a placing unit 5 for being partly inserted into the person 2 and for placing influencing elements being, in this embodiment, radiation sources close to or within the target region for directing radiation emitted by the radiation sources to the target region. The placing unit 5 is exemplarily and schematically shown in more detail in FIG. 2

The placing unit 5 comprises several introduction devices being, in this embodiment, catheters 12 for being inserted into the person 2. The placing unit 5 further comprises several navigation elements 13 being wires to which the radiation sources 10 are attached, wherein a respective wire 13 can be moved within a respective catheter 12 for placing a respective radiation source 10 at a desired placing position. The catheters 12 with the wires 13 are attached to a motor unit 14 comprising several motors for moving the wires 13 in a forward direction and in a backward direction for placing the radiation sources 10 at desired placing positions, which may also be regarded as being dwell positions. The radiation sources 10 are preferentially radioactive radiation sources emitting radioactive radiation like Ir-192. However, other radioactive sources can also be used for performing the brachytherapy.

The placing unit 5 further comprises a template 19, which can be used for inserting the catheters 12 in a more uniform configuration into the person 2. The catheters 12 are held in openings 29 in the template 19, which are arranged in a rectangular grid.

Figure 3:
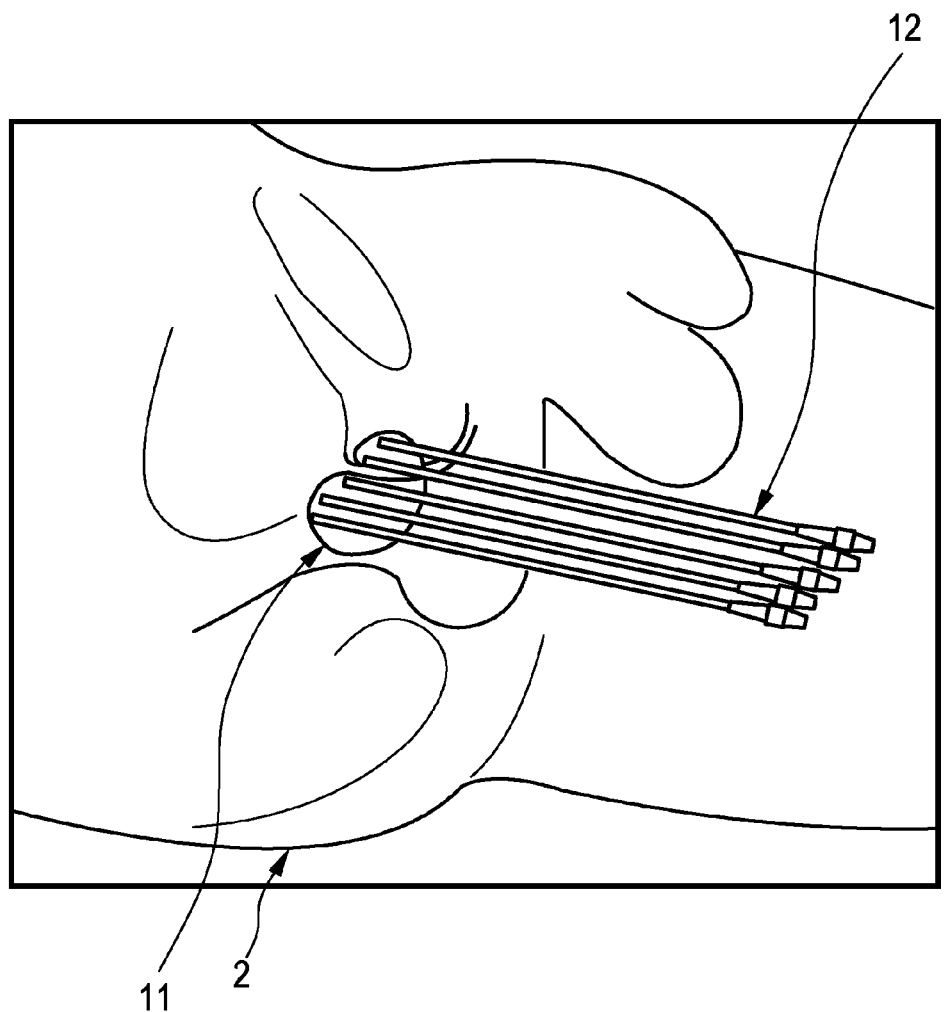
FIG. 3 shows schematically and exemplarily several catheters of the brachytherapy system inserted into the prostate of a person, FIG. 4 schematically and exemplary illustrates an arrangement of the placing unit with a TRUS probe with respect to the person, FIG. 5 schematically and exemplarily shows a calibration device together with an x-ray imaging system.

The target region is a part of the person 2 like an organ. In this embodiment, the target region is the prostate region. FIG. 3 shows schematically and exemplarily a possible arrangement of the catheters 12 of the placing unit 5 within the prostate 11.

Figure 4:
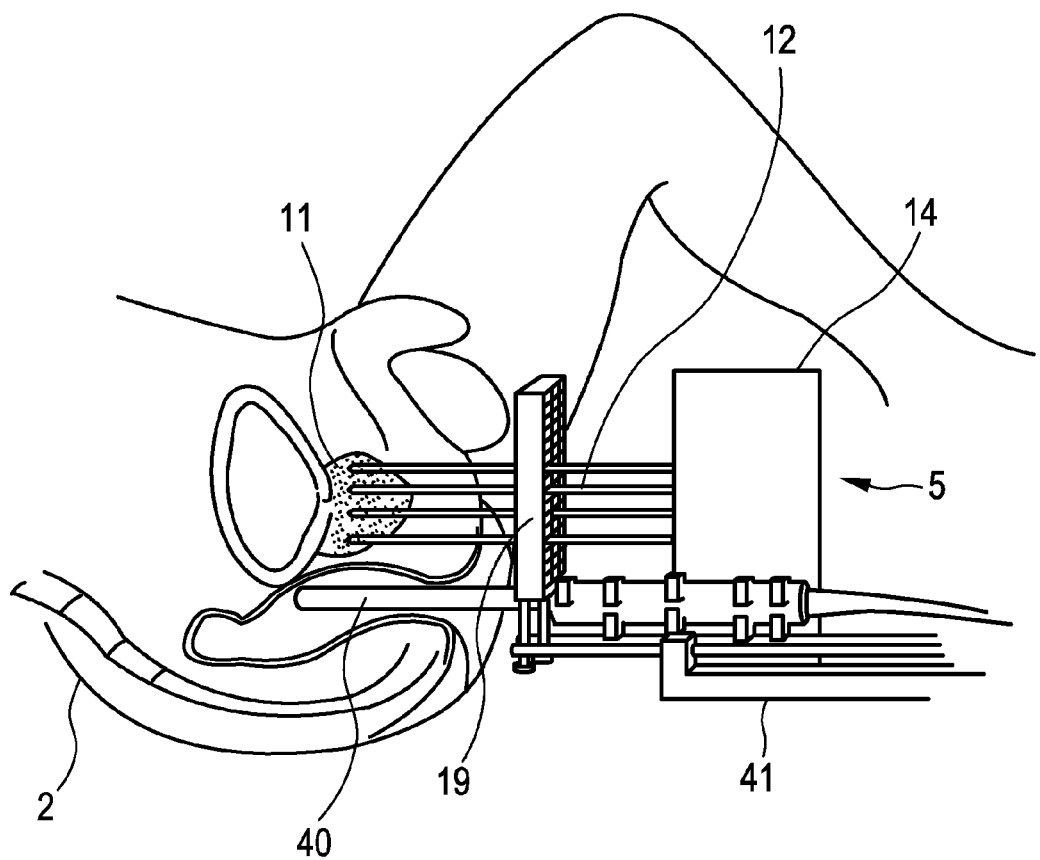

A TRUS probe 40 is attached to the placing unit 5. The arrangement of the placing unit 5 with the TRUS probe 40 during the brachytherapy is schematically and exemplarily illustrated in FIG. 4. The TRUS probe 40 and the placing unit 5 are held by a holding element 41.

The TRUS probe 40 is connected to an ultrasound control unit 42, which is located in a processing and control device 7, for generating two-dimensional or three-dimensional images of the prostate 11, which can be shown on a display 30. The ultrasound images show the catheters 12, the target region 11 being, in this embodiment, the prostate and the surrounding of the target region 11. The generated ultrasound images can therefore be used to guide the catheter implementation process, i.e. the catheters 12 can be inserted into the person 2 under ultrasound guidance.

The brachytherapy system 1 further comprises a target region pose and shape providing unit 43 for providing the pose and shape of the target region to be treated within the person 2. In this embodiment, the target region pose and shape providing unit 43 is adapted to determine the pose and shape of the target region 11 based on the ultrasound image generated by the TRUS probe 40 and the ultrasound control unit 42. In particular, the target region pose and shape providing unit 43 can be adapted to delineate the target region 11 by applying, for instance, a segmentation algorithm to the ultrasound image for completely automatically or semi-automatically delineating the target region 11 within the ultrasound image. The target region pose and shape providing unit 43 can also comprise a graphical user interface for allowing a user, which may be a radiologist, to manually delineate the target region 11, in order to determine the same. The provided pose and shape of the target region can also be shown on the display 30.

The brachytherapy system 1 further comprises an influencing plan determination unit being, in this embodiment, a treatment plan determination unit 39 for determining the treatment plan defining placing positions at which the radiation sources 10 are to be placed and placing times defining when and how long the respective radiation source 10 is to be placed at the respective placing position depending on the poses and shapes of the catheters 12, the pose and shape of the target region 11 and a spatial relation between a tracking device and a calibration element of the brachytherapy system 1, which are determined by a calibration apparatus as will be described in more detail further below.

The brachytherapy system 1 further comprises a placing control unit 15 for controlling the placing unit 5 depending on the determined treatment plan. Alternatively, the placing unit 5 may be used manually in accordance with the determined treatment plan, wherein a user may move the radiation sources 10 via the wires 13 within the catheters 12 in accordance with the treatment plan.

Before introducing the radiation sources 10 into the catheters 12, the three-dimensional poses and shapes of the catheters 12 within the person 2 are determined, i.e. the three-dimensional spatial run of each catheter 12 within the person 2 is determined. For this determination procedure the brachytherapy system 1 further comprises a tracking device 16 for being sequentially introduced into the catheters 12 and for being moved to different locations within the respective catheter 12, wherein a tracking device position providing unit 6 provides positions of the tracking device 16 at the different locations within the respective catheter 12. The positions are determined along the length of the respective catheter 12 and at a furthest position within the respective catheter 12. The furthest position within the respective catheter 12 corresponds to the position within the respective catheter 12, at which the tracking device 16 has been inserted into the respective catheter 12 as far as possible. The brachytherapy system 1 further comprises an introduction device pose and shape determination unit 44 for determining the poses and shapes of the catheters 12 from the tracked positions of the tracking device 16.

The brachytherapy system also comprises a length determination unit 45 for determining the length of the respective catheter 12 based on the tracked positions of the tracking device 16. In particular, as the tracking device 16 is retracted from the respective catheter 12, the positions of the tracking device 16 can be determined and provided to the length determination unit 45 for determining the length of the respective catheter 12 inside the person 2, i.e. distal to the grid 19, and the length of the respective catheter 12 outside the person 2, i.e. proximal to the grid 19, automatically. For determining the end of the respective catheter 12 outside of the person 2 the waviness of the tracked position data can be used by the length determination unit 45, because the waviness of the position data increases dramatically, once the tip of the tracking device 16 with the electromagnetic sensing element has exited the respective catheter 12. Alternatively, the length determination unit 45 may only determine the length of the respective catheter 12 inside the person 2, i.e. distal to the grid 19, wherein the length of the catheter 12 outside the person 2 can be measured by other conventional means.

For determining the position of the grid 19 in a coordinate system defined by the tracking system, the tip of the tracking device 16 can be arranged at the grid 19, while the position of the tip of the tracking device 16 is determined by the tracking system. After this procedure, it is known, which positions of the tip of the tracking device 16 are distal to the grid 19 and which positions of the tip of the tracking device 16 are proximal to the grid 19.

The length determined by the length determining unit 45 can be compared with a manually measured total actual length of the catheter, in order to provide a measure for the quality of the tracking system. If a difference between the manually measured total length of the catheter and the total length of the catheter determined by the length determination unit 45 is larger than a predefined threshold, the position tracking provided by the tracking device 16 should be improved.

In this embodiment the tracking device position providing unit 6 is an EM tracking unit, which cooperates with an electromagnetic sensing element arranged at the tip of the tracking device 16, which may be formed by a guidewire and the electromagnetic sensing element arranged at the tip of the guidewire. In other embodiments the tracking device position providing unit can also be adapted to track the positions of the tracking device 16 by using other tracking technologies like FOSSL.

The brachytherapy system 1 further comprises an image providing unit 8 for providing a first image showing a catheter 12 and a tracking device 16, which has been inserted into the catheter 12 as far as possible, and a second image showing the catheter 12 and a calibration element being, in this embodiment, a dummy radiation source 46, which has the same dimensions as the radiation source 10 and which has been inserted into the catheter 12 as far as possible. The first and second images are preferably, but not limited to, radiographic x-ray images, which have been generated during an initial calibration procedure, which has been performed at commissioning of the brachytherapy system 1, before the brachytherapy system had been used for the first time. In this embodiment the image providing unit 8 is a storing unit, in which these images have been stored already and from which these images can be retrieved, for providing the same. For generating these images preferentially an embodiment of a calibration device as schematically and exemplarily shown in FIG. 5 is used.

Figure 5:
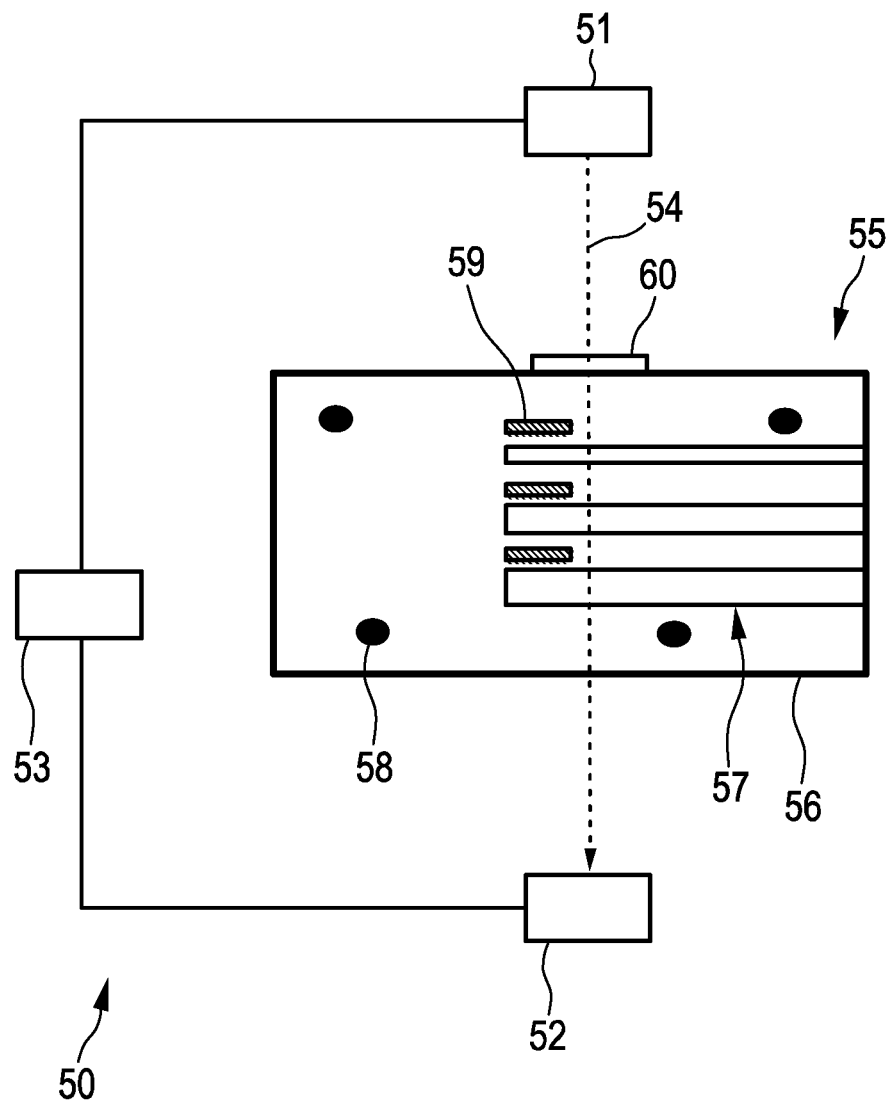

FIG. 5 schematically and exemplarily shows an embodiment of a calibration device 55 comprising a radiolucent block 56 with radiopaque fiducials identifiable in radiographic images and channels 57 for receiving a respective catheter 12. The channels 57 have different diameters, in order to allow for an accommodation of catheters having different diameters. The fiducials can be automatically detected in radiographic images. The block 56 comprises a first kind of fiducials 58 being preferentially substantially rounded, in particular, spherical, and a second kind of fiducials 59 being longish elements arranged in parallel to the channels 57. The second kind of radiopaque fiducials 59 has a known length parallel to the catheter channels 57 to relate distances measured in the image space to distances in the real physical space.

In this embodiment the block 56 further comprises an EM tracking sensor 60, which may be used together with an EM tracking system. In another embodiment another kind of tracking sensor may be used, which may be based on another tracking technology, like a FOSSL tracking sensor for spatially tracking the pose of the block 56.

The block 56 of the calibration device 55 can optionally comprise a fixing unit for fixing the respective catheter within the respective channel 57 in place. For instance, a clamping mechanism can be provided to keep inserted catheters in place.

Figure 6:
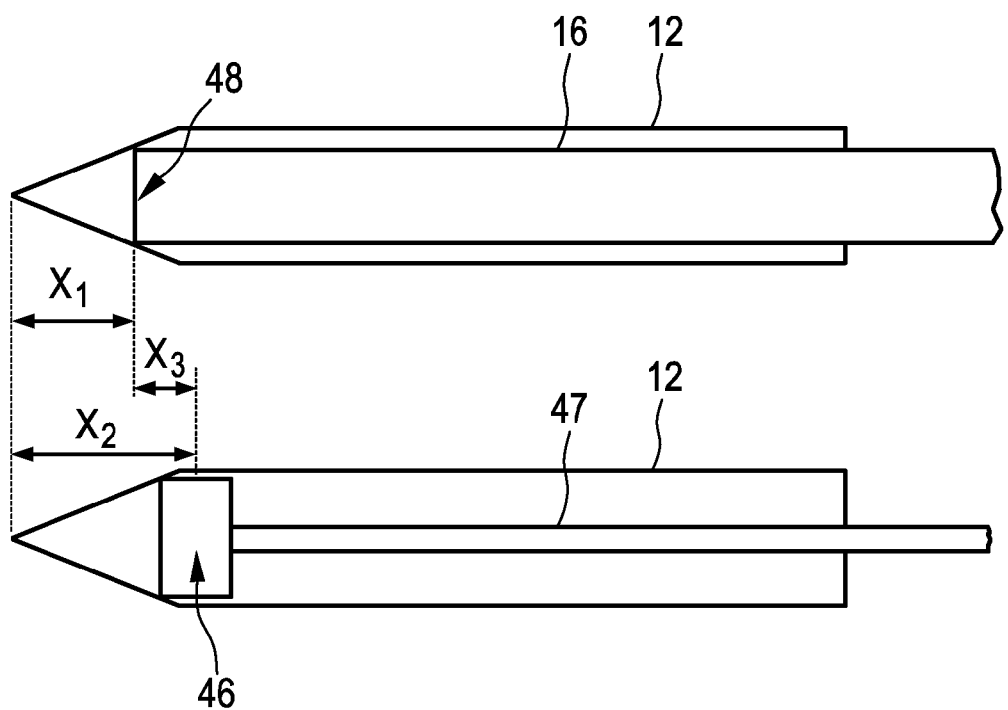
FIG. 6 illustrates several distances determined during a calibration procedure.

For calibrating the brachytherapy system a catheter 12 is inserted into one of the channels 57 of the block 56, wherein into the respective catheter, which has been inserted into the respective channel, a tracking device or a dummy radiation source is inserted as far as possible as schematically and exemplarily shown in FIG. 6.

Referring again to FIG. 5, an x-ray imaging system 50 is used for generating the first and second images. The x-ray imaging system 50 comprises an x-ray source 51 for emitting x-ray radiation substantially in the direction indicated by the arrow 54 and an x-ray detector 52 for detecting the x-ray radiation, after having traversed the calibration device 55. Signals being indicative of the detected x-ray radiation are provided to an x-ray control unit 53, which is adapted to generate an x-ray image based on the provided signals. The x-ray control unit 53 also controls the emission and detection of the x-ray radiation. In particular, a first x-ray image is generated, after a catheter 12 with a tracking device 16 has been inserted into a channel 57 of the calibration device 55 as shown in the upper part of FIG. 6 and a second x-ray image is generated, after a catheter 12 with a dummy radiation source 46 has been inserted into a channel 57 of the brachytherapy device 55 as shown in the lower part of FIG. 6. The dummy radiation source 46 has been moved to the furthest position within the catheter 12 by using a navigation element 47 being preferentially a guidewire.

The EM tracking sensor 60 is preferentially arranged such that it appears in an x-ray image generated by the x-ray imaging system 50, in order to relate the coordinate system of the x-ray imaging system 50 and of the EM tracking system to one another. After these two coordinate systems have been related to each other, spatial relationships between the EM tracking sensor 60 and the channels 57 can be determined from an x-ray image and these spatial relations can be compared with further spatial relations between the EM tracking sensor 60 and the catheter, after it has been inserted into a channel 57, determined by using the EM tracking system, in order to provide a further quality assurance of the EM tracking system with respect to its ability to be used for estimating the pose, shape and tip position of the catheter. This comparison can be used for validating the accuracy of the EM readings reported by the EM tracking system during an additional TRUS-EM quality assurance procedure, which will be described further below.

The brachytherapy system 1 further comprises an identification unit 70 for identifying the tip of the catheter 12, the tip 48 of the tracking device 16 and the dummy radiation source 46 in the first and second images. The brachytherapy system 1 also comprises a spatial relation determining unit 71 for determining spatial relations between positions of the tip of the catheter 12, the tip 48 of the tracking device 16 and the dummy radiation source 46 from the first and second images, in which the catheter 12, the tip 48 of the tracking device 16 and the dummy radiation source 46 have been identified. The identification unit 70 can be adapted to automatically identify the tip of the catheter 12, the tip 48 of the tracking device 16 and the dummy radiation source 46 or to allow a user to identify these elements in the images. For automatically detecting these elements, known segmentation techniques, which may be based on thresholding, can be used.

The spatial relation determining unit 71 is adapted to determine i) the distance $X_1$ between the position of the tip of the catheter 12 and the position of the tip 48 of the tracking device 16, ii) the distance $X_2$ between the position of the tip of the catheter 12 and the position of the dummy radiation source 46 and iii) the distance $X_3$ between the position of the tip 48 of the tracking device 16 and the position of the dummy radiation source 46. The distance $X_3$ is determined by subtracting the other distances $X_2$ and $X_1$ from each other.

The identification unit and the spatial relation determining unit may be implemented as software components running on a workstation for performing the image processing and calculation procedures. Thus, a software can be provided that allows importing the first and second radiographic images showing the catheter 12 inserted into the channel 57 of the block 56 with either a tracking device 16 or a dummy radiation source 46, wherein the catheter tips, the tip of the tracking device and the dummy radiation source can be manually or automatically identified in the first and second images and wherein the differences in the positions can be calculated, in particular, wherein the distance $X_3$ can be calculated. At least this spatial relation $X_3$ is then provided to the treatment plan determination unit 39 for allowing the treatment plan determination unit 39 to determine the treatment plan depending—inter alia—on this spatial relation.

After the initial calibration, which has been performed before the brachytherapy system 1 or parts of the brachytherapy system 1 like the catheters 12, the tracking device 16 and/or the radiation source 10, are used for the first time, and after the calibration system has been used several times, the initially determined spatial relations may not correspond anymore to the real spatial relations between the different components of the brachytherapy system. For instance, after the brachytherapy system 1 has been used several times, the initially determined distance $X_3$ may not correspond anymore to the actual distance between the furthest position of the tip of the tracking device 16 within the respective catheter 12 and the furthest position of the radiation source 10 within the respective catheter 12. This change of the spatial relations over time may be caused by, for instance, mechanical wear and tear or other physical changes occurring over time, wherein these changes may result in interfacing errors between navigation, planning and delivery components of the brachytherapy system.

For this reason the brachytherapy system is adapted to allow for a quality assurance procedure, which may be performed on a periodic basis. For instance, the quality assurance procedure may be performed every three months or every year. In particular, the ultrasound image providing unit 40, 42, i.e. in this embodiment the TRUS probe and the ultrasound control unit, may be adapted to provide an ultrasound image of the tip of the catheter 12, while the tracking device 16 has been inserted into the catheter 12 as far as possible. In this situation the identification unit 70 may identify the tip of the catheter 12 in the ultrasound image and the tracking device position providing unit 6 may determine the furthest position of the tip of the tracking device 16 within the catheter 12. Based on these two positions the spatial relation determination unit 71 may update the distance $X_1$, which in turn may be used to recalculate the distance $X_3$, wherein in this example it is assumed that the distance $X_2$ did not change over time. The updated spatial relations, in particular, the corrected distance $X_3$, can be provided to the treatment plan determination unit 39 for allowing the treatment plan determination unit 39 to determine the treatment plan for a next brachytherapy depending on inter alia the updated distance $X_3$.

For performing this quality assurance procedure the calibration device 55 described above with reference to FIG. 5 may be used, wherein in this case the calibration device 55 is adapted to be TRUS-compatible, i.e. the composition of the radiolucent block 56 preferentially mimics the acoustic properties of tissue. Alternatively, for the quality assurance procedure, a commercially available ultrasound phantom may be used, which has acoustic properties being similar to the acoustic properties of tissue.

Moreover, the quality assurance procedure may also be performed, after a catheter has been inserted into the person 2, by using the tracking device 16 and the TRUS probe 40, i.e. the quality assurance procedure may also be performed intra-procedurally on the person.

The treatment plan determining unit 39 is adapted to determine the treatment plan depending on the poses and shapes of the catheters 12, after they have been introduced into the person 2, depending on the determined pose and shape of the target region 11, on the actually determined furthest position of the tip of the tracking device 16 within the respective catheter 12 and depending on the distance $X_3$ determined in the initial calibration step, wherein this distance $X_3$ may have been updated in a subsequent quality assurance procedure. For planning the different placing positions and corresponding placing times known planning techniques can be used like the planning technique disclosed in the article "Optimization of HDR brachytherapy dose distributions using linear programming with penalty costs" by Ron Alterovitz et al., Medical Physics, volume 33, number 11, pages 4012 to 4019, November 2006, which is herewith incorporated by reference. The planning techniques particularly use the distance $X_3$ for determining the first dwell position of the radiation source, which is preferentially used as a reference point in a coordinate system of the placing unit 5, which can be regarded as being an afterloader unit.

Figure 7:
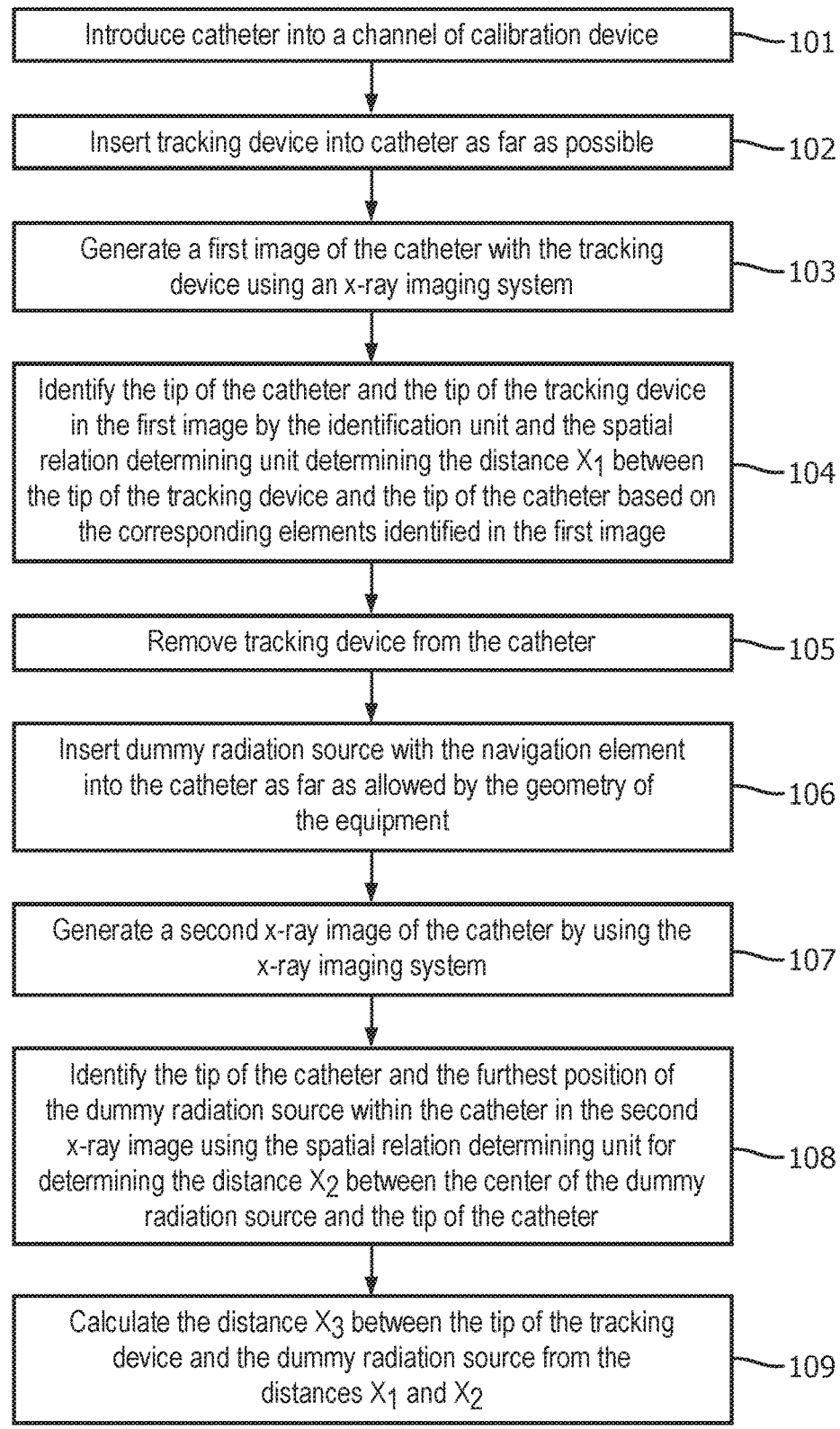
FIG. 7 shows a flowchart exemplarily illustrating an embodiment of a calibration method, FIG. 8 exemplarily shows a further flowchart illustrating a quality assurance procedure of the calibration method, FIG. 9 schematically and exemplarily shows an embodiment of a calibration apparatus.

In the following a calibration method for calibrating a brachytherapy system 1 will exemplarily be described with reference to a flowchart shown in FIG. 7.

In step 101 a catheter 12 is introduced into a channel 57 of the calibration device 55, wherein in step 102 a tracking device 16 is inserted into the catheter 12 as far as possible. In particular, the tracking device 16 may comprise an electromagnetic sensing element at the tip of a guidewire of the tracking device, wherein the guidewire with the electromagnetic sensing element is completely inserted into the catheter 12 and held in place. In step 103 a first image of the catheter 12 with the tracking device 16 is generated by using the x-ray imaging system 50. In particular, a first x-ray image is obtained, which shows the catheter 12 containing a guidewire with the electromagnetic sensing element forming the tracking device. In step 104 the tip of the catheter 12 and the tip of the tracking device 16 are identified in the first image by the identification unit 70 and the spatial relation determining unit 71 determines the distance $X_1$ between the tip of the tracking device 16 and the tip of the catheter 12 based on the corresponding elements identified in the first image. Thus, for instance, the distance $X_1$ between the tip of a guidewire, at which an electromagnetic sensing element may be present, and a catheter tip is calculated. In step 105 the tracking device 16 is removed from the catheter 12 and in step 106 the dummy radiation source 46 with the navigation element 47 is inserted into the catheter 12 as far as allowed by the geometry of the equipment. The dummy radiation source 46 has dimensions, which are identical to the dimensions of an actual radiation source that will be used in the brachytherapy. Then, in step 107 a second x-ray image of the catheter 12 is generated by using the x-ray imaging system 50, wherein in step 108 the tip of the catheter 12 and the furthest position of the dummy radiation source 46 within the catheter 12 are identified in the second x-ray image and used by the spatial relation determining unit 71 for determining the distance $X_2$ between the center of the dummy radiation source 46 and the tip of the catheter 12. In step 109 the distance $X_3$ between the tip of the tracking device 16, in particular, of the tip 48 of the guidewire 16, and the dummy radiation source 46, in particular the center of the dummy radiation source 46, is calculated from the distances $X_1$ and $X_2$.

Although in the embodiment of the calibration method described above with reference to FIG. 7 a certain sequence of steps is shown, the sequence of steps can also be different. For instance, firstly the first and second images can be generated, which show the catheter tip with the tracking device and the catheter tip with the dummy radiation source, respectively, wherein then in both images the respective elements can be identified and used for determining the distances $X_1$ and $X_2$ and finally $X_3$. Thus, for instance, steps 102, 103 and 105 to 107 can be performed before steps 104, 108 and 109.

Figure 8:
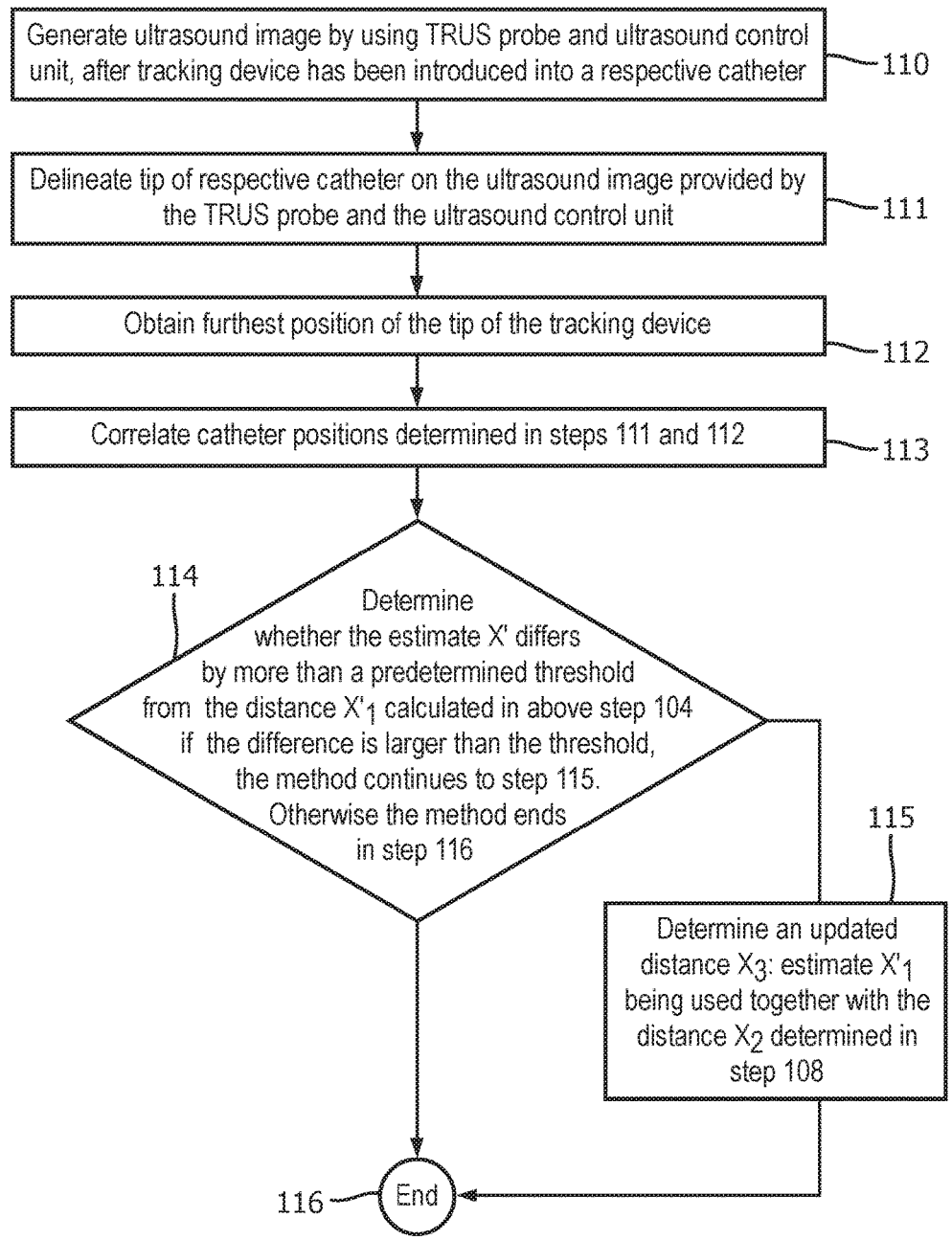

Steps 101 to 109 may be performed for initially calibrating the brachytherapy system 1, before the brachytherapy system 1 or parts of the brachytherapy system 1 are used for the first time. The calibration method can comprise further steps, which are performed later, after the brachytherapy system 1 has been used several times, for performing a quality assurance procedure. Preferred corresponding steps of the calibration method, which can be carried out for performing a corresponding quality assurance procedure, will in the following be described with reference to the flowchart shown in FIG. 8.

In step 110 an ultrasound image is generated by using the TRUS probe 40 and the ultrasound control unit 42, after the tracking device 16 has been introduced into a respective catheter 12. In step 111 the tip of the respective catheter 12 is delineated on the ultrasound image provided by the TRUS probe 40 and the ultrasound control unit 42. This delineation may be performed by the identification unit 70. In step 112 the furthest position of the tip of the tracking device 16, i.e. in this embodiment the EM-reported position of the tip of the respective catheter, is obtained from the tracking device position providing unit 6. If several catheters 12 are present, these positions are determined for each catheter, wherein, if only a single tracking device 16 is present, the tracking device 16 may be sequentially inserted into the different catheters 12, in order to determine the furthest positions of the tip of the tracking device 16 in the different catheters 12. In step 113 for each catheter 12 the positions determined in steps 111 and 112 are correlated, in order to determine an estimation $X'_1$ for the distance between the tip of the respective catheter and the furthest position of the tracking device within the respective catheter. This determination of the estimate $X'_1$ can be performed by the spatial relation determination unit 71. In step 114 it is determined whether the estimate $X'_1$ differs by more than a predetermined threshold from the distance $X_1$ calculated in above step 104, wherein, if the difference is larger than the threshold, the method continues with step 115. Otherwise the method ends in step 116. In step 115 the estimate $X'_1$ is used together with the distance $X_2$ determined in step 108 for determining an updated distance $X_3$.

For performing this quality assurance procedure, a phantom may be used, which is TRUS-compatible and which is compatible to the used tracking technology, in particular, to EM-tracking. Also the calibration device 55 described above with reference to FIG. 5 may be used for the quality assurance procedure, if the calibration device 55 is TRUS-compatible and compatible for the respective tracking technology. Moreover, the quality assurance procedure may also be performed, after the catheters have been inserted into the person 2, i.e. the quality assurance procedure may be performed intra-procedurally.

Also the steps described above with reference to FIG. 8 may be performed in another sequence. For instance, step 112 may be performed before steps 110 and 111.

Figure 9:
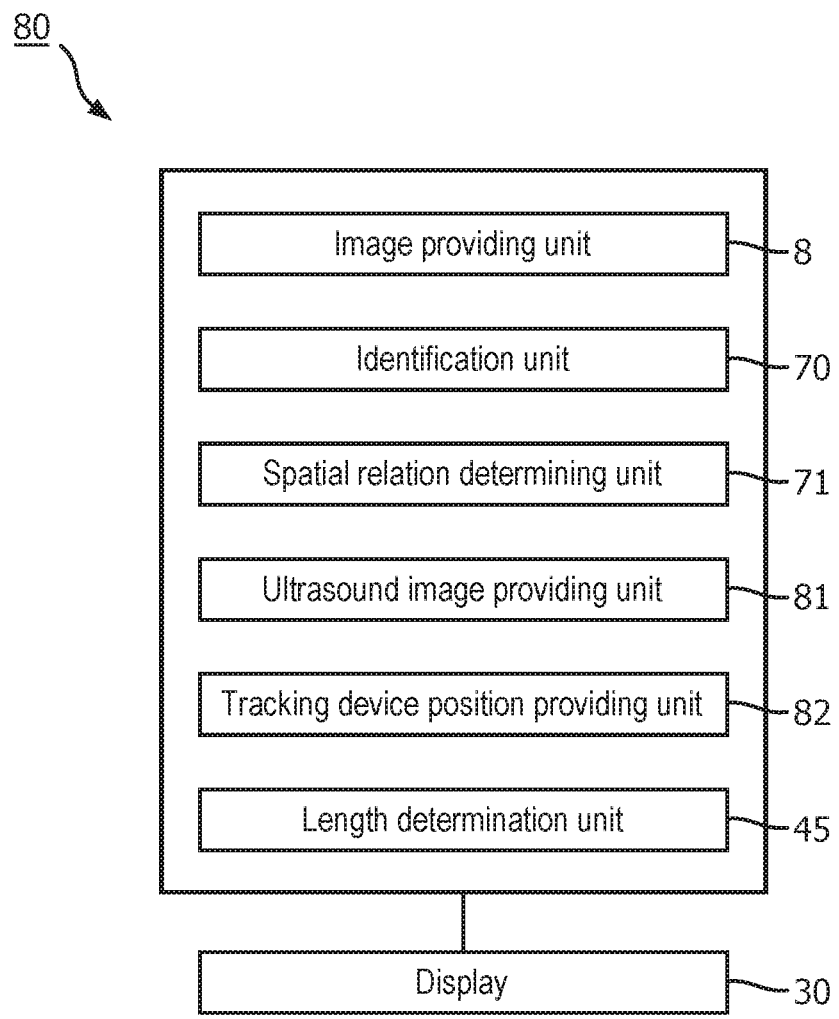

The units needed for performing the calibration method described above with reference to FIGS. 7 and 8 can be integrated into the brachytherapy system 1 as shown in FIG. 1 or they can form a separate apparatus, which is connected to the brachytherapy system for interfacing the determined spatial relations to the brachytherapy system. A corresponding calibration apparatus 80 is schematically and exemplarily shown in FIG. 9.

The calibration apparatus 80 comprises an image providing unit 8 for providing first and second images showing the respective catheter tip with the respective tip of the tracking device and the respective catheter tip with the dummy radiation source, respectively. In this embodiment, the image providing unit 8 is a receiving unit for receiving the first and second images from an image generation system like the x-ray imaging system 50, wherein the image providing unit 8 is adapted to provide the received first and second images.

The calibration apparatus 80 further comprises an identification unit 70, a spatial relation determining unit 71 and a length determination unit 45, which are similar to the corresponding units described above with reference to FIG. 1. Moreover, the calibration apparatus 80 comprises an ultrasound image providing unit 81 and a tracking device position providing unit 82. Both units are receiving units for receiving the respective information, i.e. the ultrasound image and the furthest position of the tracking device, wherein the ultrasound image providing unit 81 is adapted to provide the received ultrasound image and wherein the tracking device position providing unit 82 is adapted to provide the received furthest tracking device position. The ultrasound image providing unit 81 is adapted to provide the ultrasound image used for performing the above described quality assurance procedure.

Also the calibration apparatus 80 can comprise a display 30. The display 30 can show, for instance, the images, positions and distances.

Figure 10:
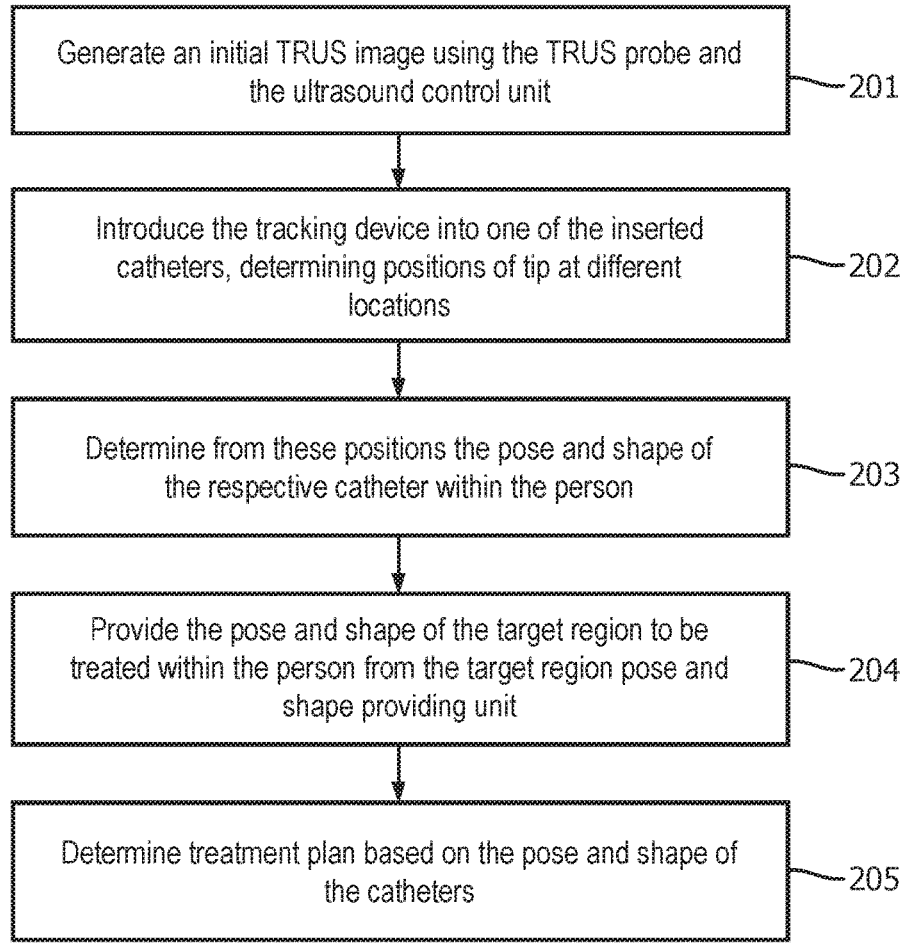
FIG. 10 shows a flowchart exemplarily illustrating an embodiment of a treatment plan determination method, and FIG. 11 schematically and exemplarily shows an embodiment of a treatment plan determination apparatus.

In the following an embodiment of a treatment plan determination method will exemplarily be described with reference to a flowchart shown in FIG. 10.

In step 201 an initial TRUS image is generated by the TRUS probe 40 and the ultrasound control unit 42, wherein the generated image shows the target region 11 within the person 2. Moreover, the template 19 is placed adjacent to the person 2 such that the catheters 12 can be introduced through the openings 29 in the template 19 into the target region 11 of the person 2 under ultrasound guidance. In step 202 the tracking device 16 is introduced into one of the inserted catheters 12, wherein during this introduction of the tracking device 16 the tip of the tracking device 16 is moved along different locations within the respective catheter 12 and the positions of the tip of the tracking device 16 at the different locations are determined. Moreover, when the tracking device 16 has reached the furthest position within the respective catheter 12, also this position is determined. In step 203 these positions are used to determine the pose and shape of the respective catheter 12 within the person 2. For instance, the determined positions, which are arranged along a line describing the pose and shape of the respective catheter 12, can directly define the pose and shape of the respective catheter 12 such that the sequence of acquired determined positions of the tracking device 16 can directly be regarded as being the determined pose and shape of the respective catheter 12. Steps 202 and 203 are performed for each catheter 12 inserted into the person 2, in order to determine for each catheter 12 the pose and shape within the person 2.

In step 204 the pose and shape of the target region 11 to be treated within the person 2 is provided by the target region pose and shape providing unit. In particular, the TRUS image is used for determining the pose and shape of the target region 11 by applying, for instance, a segmentation algorithm to the TRUS image. In step 205 the treatment plan is determined based on the pose and shape of the catheters 12, the pose and shape of the target region 11, the furthest position of the tracking device 16 within the respective catheter 12 and the distance $X_3$ determined in the initial calibration procedure, wherein this distance $X_3$ may have been updated in a later quality assurance procedure. The determined treatment plan can be used by the brachytherapy system 1 for moving radiation sources within the catheters 12 in accordance with the treatment plan.

Figure 11:
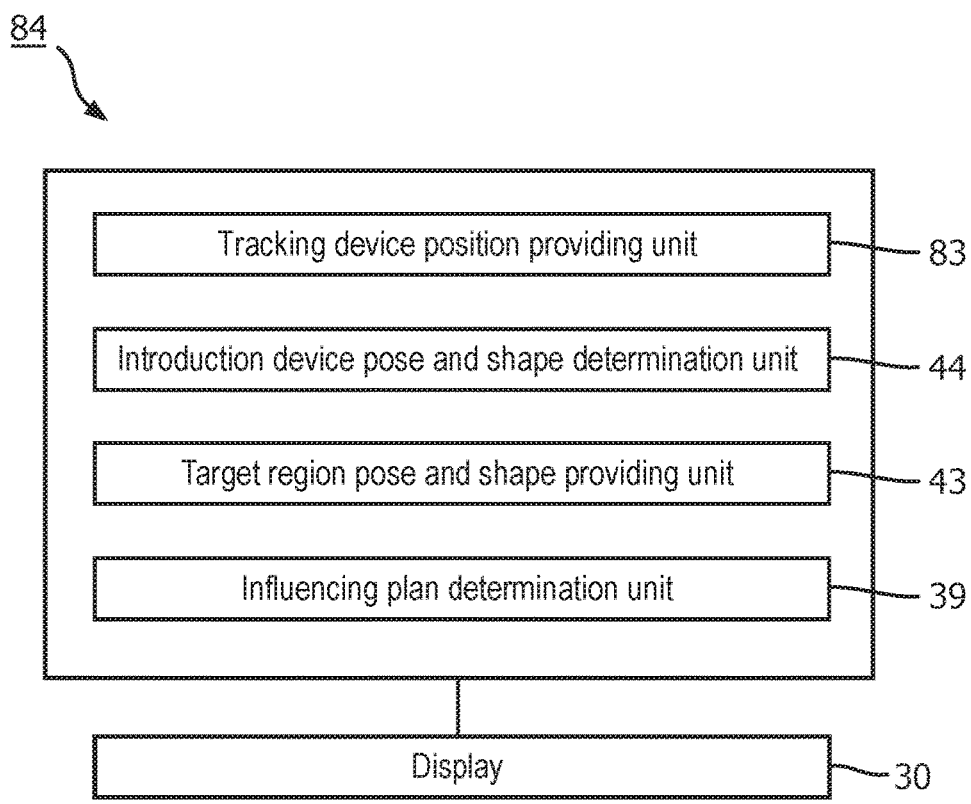

The tracking device position providing unit 6, the introduction device pose and shape determination unit 44, the target region pose and shape providing unit 43 and the treatment plan determination unit 39 described above with reference to, for instance, FIG. 1, can be regarded as forming a treatment determination apparatus for determining a treatment plan for a brachytherapy, which is integrated with the brachytherapy system. In other embodiments the treatment plan determination apparatus can also be a separate apparatus for determining a treatment plan for a brachytherapy, wherein the determined treatment plan is transferred to the brachytherapy system for performing the brachytherapy in accordance with the treatment plan. Such a separate treatment plan determination apparatus is schematically and exemplarily shown in FIG. 11.

The treatment plan determination apparatus 84 comprises a tracking device position providing unit 83 for providing positions of the tracking device 16 within the respective catheter 12, wherein the positions are determined along the length of the respective catheter 12. The tracking position providing unit 83 is further adapted to provide the furthest position of the tracking device 16 within the respective catheter 12. In this embodiment the tracking device position providing unit 83 is adapted to receive tracked positions of the tracking device 16 and to provide these received tracked positions. The treatment plan determination apparatus 84 further comprises the introduction device pose and shape determination unit 44, the target region pose and shape providing unit 43 and the treatment plan determination unit 39 described above with reference to FIG. 1. Moreover, also the treatment plan determination apparatus 84 comprises a display 30 for displaying, for instance, the provided positions, poses and shapes.

The brachytherapy is preferentially adapted to perform a HDR brachytherapy as a form of cancer therapy that utilizes high doses of ionizing radiation delivered over a short period of time in the order of some minutes directly at or near the target. Due to the high dose delivery rates involved the margin of error is minimal. It is therefore important to be not only able to develop an accurate treatment plan, but also to deliver radiation accurately according to the developed treatment plan. In order to obtain an accurate treatment plan and correspondingly an accurate brachytherapy procedure, the brachytherapy system is preferentially adapted to provide a spatial registration for enabling a seamless use of, for instance, the EM tracking technology in brachytherapy planning and delivery.

In particular, the brachytherapy system is preferentially adapted to provide an image-based technology for correlating the positions of the catheter tip, the furthest achievable position of an EM tracker inside the respective catheter and the furthest achievable position of a dummy radiation source inside the respective catheter, wherein radiographic imaging techniques are preferentially used to determine these positions. The spatial offsets between each of these quantities is preferentially determined and accounted for, when computing and executing the treatment plan. These spatial offsets are preferentially initially calculated, when the equipment is deployed for the first time. These measurements and determinations of the spatial offsets can therefore also be regarded as being baseline measurements or commissioning measurements. The brachytherapy system is preferentially further adapted to perform periodically a quality assurance procedure, during which offsets can be recalculated as needed and compared to the baseline or commissioning measurements.

For performing the quality assurance procedure preferentially spatial relationships between TRUS-estimated catheter tips and EM-estimated catheter tips, i.e. the furthest positions of the tip of the tracking device, are quantified for use in EM-TRUS clinical workflows.

The brachytherapy system described above with reference to FIG. 1 is preferentially adapted to perform a HDR brachytherapy. However, in other embodiments the brachytherapy system may also be adapted to perform another kind of brachytherapy. Moreover, in above described embodiments, the brachytherapy system is adapted to treat the prostate of a person. In other embodiments the brachytherapy system can be adapted to treat other parts of a living object like other organs.

Although in above described embodiments TRUS imaging has been used for different purposes during the entire brachytherapy procedure, for instance, for guiding the insertion of the catheters, for performing the quality assurance procedure, et cetera, also other imaging techniques can be used for these purposes. For instance, another kind of ultrasound imaging, computed tomography imaging et cetera can be used.

Although in above described embodiments the radiography-based calibration procedure is determined only initially, before the respective equipment is used for the first time, in other embodiments this procedure can be performed at periodic intervals repeatedly, in order to update the results of the initial calibration procedure.

Although in above described embodiments the system for introducing an influencing element into an object, wherein the influencing element is adapted to influence a target region within the object, is a brachytherapy system, wherein the influencing element is a radiation source and wherein the influencing plan is a brachytherapy treatment plan, in other embodiments the system can also be adapted to introduce another kind of influencing element into the object. For instance, the system can be adapted to perform another interventional procedure using a working channel in which a tracking device like an EM tracking device or an FOSSL tracking device is initially inserted to determine the pose and shape of the working channel, wherein then the influencing element, which may be regarded as being a therapy delivery device like a stent, an ablation needle, et cetera, may be inserted into the working channel to deliver the therapy.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the identification of the tip of the catheter, of the tip of the tracking device and of the dummy radiation source in the first and second images, the determinations of the spatial relations between these elements, the determination of the total length of a catheter, the determination of the poses and shapes of the catheters, the determination of the pose and shape of a target region, the determination of a treatment plan, et cetera performed by one or several units or devices can be performed by any other number of units or devices. These procedures and/or the control of the calibration apparatus in accordance with the calibration method and/or the control of the treatment plan determination apparatus in accordance with the treatment plan determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a calibration apparatus for calibrating a system for introducing an influencing element like a radiation source into an object, particularly for calibrating a brachytherapy system. First and second images show a longish introduction device like a catheter and a tracking device like an electromagnetically trackable guidewire inserted into the introduction device as far as possible, and the introduction device and a calibration element having the same dimensions as the influencing element and being inserted into the introduction device as far as possible. A spatial relation between the tracking device and the calibration element is determined based on the images for calibrating the system. Knowing this spatial relation allows accurately determining an influencing plan like a brachytherapy treatment plan and accurately positioning the influencing element in accordance with the influencing plan, which in turn allows for a more accurate influencing of the object.

The invention claimed is:
1. A calibration apparatus for calibrating a system for introducing an influencing element into an object, wherein the influencing element is adapted to influence a target region within the object and wherein the calibration apparatus comprises:
   an image providing unit for providing a first image showing a longish introduction device, which is adapted to be inserted into the object for introducing the influencing element into the object, and a tracking device, which is adapted to track the introduction device and to be inserted into the introduction device as far as possible, and a second image showing the introduction device and a calibration element, which has the same dimensions as the influencing element and which is to be inserted into the introduction device as far as possible;

an identification unit for identifying the tip of the introduction device, the tracking device and the calibration element in the first and second images; and a spatial relation determining unit for determining a spatial relation between the tracking device and the calibration element from the first and second images, in which the tip of the introduction device, the tracking device and the calibration element have been identified.

2. The calibration apparatus as defined in claim 1, wherein the spatial relation determining unit is adapted to determine:
   a distance between the position of the tip of the introduction device and the position of the tracking device from the first image, in which the tip of the introduction device and the tracking device have been identified,
   a distance between the position of the tip of the introduction device and the position of the calibration element from the second image, in which the tip of the introduction device and the calibration element have been identified, and
   a distance between the position of the tracking device and the position of the calibration element based on the determined the distance between the position of the tip of the introduction device and the position of the tracking device and the distance between the position of the tip of the introduction device and the position of the calibration element.

3. The calibration apparatus as defined in claim 1, wherein the calibration apparatus further comprises:
   an ultrasound image providing unit for providing an ultrasound image of the tip of the introduction device; and
   a tracking device position providing unit for providing a position of the tracking device, when it has been inserted into the introduction device as far as possible, wherein the identification unit is adapted to identify the tip of the introduction device in the ultrasound image and wherein the spatial relation determination unit is adapted to update the spatial relation between the tracking device and the calibration element based on the ultrasound image with the identified tip of the introduction device and the provided position of the tracking device.

4. The calibration apparatus as defined in claim 3, wherein the tracking device position providing unit is adapted to provide an electromagnetically or fiber optically shaped sensing tracked position of the tracking device.

5. The calibration apparatus as defined in claim 3, wherein the tracking device position providing unit is adapted to provide the positions of the tracking device, while it is moved inside the introduction device towards and/or away from a furthest position within the introduction device, and wherein the calibration apparatus further comprises a length determination unit for determining a length of the introduction device based on the provided positions.

6. The calibration apparatus as defined in claim 1, wherein the image providing unit is adapted to provide radiographic images as the first and second images.

7. The calibration apparatus as defined in claim 1, further comprising a calibration device that comprises a radiolucent block with
   radiopaque fiducials identifiable in radiographic images, and
   a channel for receiving an introduction device that is adapted to be inserted into the object for introducing an influencing element into the object.

8. The calibration apparatus as defined in claim 7, wherein at least some of the fiducials are arranged in parallel to the channel.

9. The calibration apparatus as defined in claim 7, wherein the block comprises several channels having different diameters.

10. The calibration apparatus as defined in claim 7, wherein the block is ultrasound compatible.

11. An influencing plan determination apparatus incorporating the calibration apparatus as defined in claim 1 and for determining an influencing plan for influencing a target region within an object, the influencing plan determination apparatus comprising:
    a tracking device position providing unit for providing positions of a tracking device within an introduction device, which has been inserted into the object for introducing an influencing element into the object, wherein the positions are determined along the length of the introduction device and at a furthest position within the introduction device;
    an introduction device pose and shape determination unit for determining the pose and shape of the introduction device from the provided positions of the tracking device;
    a target region pose and shape providing unit for providing the pose and shape of the target region within the object; and
    an influencing plan determination unit for determining the influencing plan depending on the pose and shape of the introduction device, the pose and shape of the target region, the furthest position of the tracking device within the introduction device and the spatial relation between the tracking device and the calibration element determined by the calibration apparatus.

12. A calibration method for calibrating a system for introducing an influencing element into an object, wherein the influencing element is adapted to influence a target region within the object and wherein the calibration method comprises:
    providing a first image showing a longish introduction device, which is adapted to be inserted into a living object for introducing an influencing element within the living object, and a tracking device, which is adapted to track the introduction device and which inserted into the introduction device as far as possible, and a second image showing the introduction device and a calibration element, which has the same dimensions as the influencing element and which is inserted into the introduction device as far as possible, by an image providing unit;
    identifying the tip of the introduction device, the tracking device and the calibration element in the first and second images by an identification unit; and
    determining a spatial relation between the tracking device and the calibration element from the first and second images, in which the introduction device, the tracking device and the calibration element have been identified, by a spatial relation determining unit.

13. An influencing plan determination method incorporating the calibration method as defined in claim 12 and for determining an influencing plan for influencing a target region within an object, the influencing plan determination method comprising:

providing positions of a tracking device within an introduction device, which has been inserted into the object for introducing an influencing element into the object, by a tracking device position providing unit, wherein the positions have been determined along the length of the introduction device and at a furthest position within the introduction device, determining the pose and shape of the introduction device from the provided positions of the tracking device by an introduction device pose and shape determination unit, providing the pose and shape of the target region within the object by a target region pose and shape providing unit, determining the influencing plan depending on the pose and shape of the introduction device, the pose and shape of the target region, the furthest position of the tracking device within the respective introduction device and the spatial relation between the tracking device and the calibration element determined by the calibration method.

14. A non-transitory computer readable medium embodied with a computer program for calibrating a system for introducing an influencing element into an object, wherein the influencing element is adapted to influence a target region within the object, the calibration computer program comprising executable program code for causing a calibration apparatus as defined in claim 1 to carry out the steps of a calibration method, when the computer program is executed on a computer controlling the calibration apparatus.

15. A non-transitory computer readable medium embodied with a computer program for determining an influencing plan for influencing a target region within an object, the influencing plan determination computer program comprising executable program code for causing an influencing plan determination apparatus as defined in claim 11 to carry out the steps of an influencing plan determination method, when the influencing plan determination computer program is executed on a computer controlling the influencing plan determination apparatus.

* * * * *